United States Patent [19]

Shih

[11] Patent Number: 5,107,002
[45] Date of Patent: Apr. 21, 1992

[54] LOWER ALKYLENE OXIDE PURIFICATION

[75] Inventor: T. Thomas Shih, Bryn Mawr, Pa.

[73] Assignee: Arco Chemical Technology, L.P., Wilmington, Del.

[21] Appl. No.: 623,007

[22] Filed: Dec. 6, 1990

[51] Int. Cl.$^5$ .......................................... C07D 301/32
[52] U.S. Cl. .................................. 549/542; 549/512; 549/513; 549/541
[58] Field of Search ............... 549/513, 512, 542, 541; 560/129; 203/60

[56] References Cited

U.S. PATENT DOCUMENTS 3,629,144 12/1971 Hahn et al. ........................ 549/542
4,772,732 9/1988 Huang et al. ...................... 549/542

FOREIGN PATENT DOCUMENTS 60-199019A 10/1985 Japan .................................. 549/542

Primary Examiner—Glennon H. Hollrah
Assistant Examiner—S. Kumar
Attorney, Agent, or Firm—William C. Long

[57] ABSTRACT

The method for the separating methyl formate from lower alkylene oxide such as propylene oxide which comprises contacting the impure alkylene oxide with basic ion exchange resin and separating alkylene oxide reduced in methyl formate content.

8 Claims, No Drawings

1

LOWER ALKYLENE OXIDE PURIFICATION

BACKGROUND OF THE INVENTION

1. Field of the Invention

The present invention relates to the separation of methyl formate from lower alkylene oxides such as propylene oxide by treatment with basic ion exchange resin.

2. Description of the Prior Art

Monoepoxides such as propylene oxide are highly important chemicals useful in a great number of applications. An important commercial technology for producing the monoepoxides is via the catalytic reaction between the corresponding olefin and an organic hydroperoxide, the hydroperoxide being prepared by hydrocarbon oxidation. See, for example, U.S. Pat. No. 3,351,635.

The epoxide product mixtures contain impurities such as methyl formate which are difficult to separate due to very small differences in boiling point between the epoxide and the impurities. In the case of propylene oxide, for example, considerable effort has been devoted to separating the close boiling methyl formate and other impurities.

One direction taken by prior workers has been to provide extractive distillation techniques to accomplish the separation. U.S. Pat. No. 3,838,020 shows a dual solvent extractive distillation process. U.S. Pat. No. 3,843,488 shows extraction distillation using a $C_8$ to $C_{20}$ hydrocarbon to purify propylene oxide. U.S. Pat. No. 3,909,366 shows extractive distillation purification of propylene oxide using $C_6$ to $C_{12}$ aromatic hydrocarbon. U.S. Pat. No. 4,140,588 uses water in extractive distillation purification of propylene oxide. U.S. Pat. No. 3,881,996 uses plural stage distillation to purify propylene oxide. East German Patent Specification uses aliphatic alcohols such as tertiary butanol in separating methyl formate from propylene oxide by extractive distillation. Co-pending application Ser. No. 07/491,872 filed Mar. 12, 1990 uses tertiary butyl alcohol and water in the extractive distillation purification of propylene oxide.

It has previously been proposed to separate oxygen-containing impurities from the propylene oxide by extractive distillation using lower glycols such as ethylene glycol and propylene glycol. See U.S. Pat. No. 3,578,568 which describes this procedure and which teaches use of solvent in amount to comprise 15 to 50% of the vapor space in the distillation zone. Copending application Ser. No. 07/327,876 filed Mar. 17, 1989 describes a similar separation but one which uses much lower solvent concentrations whereby propylene oxide losses are reduced.

U.S. Pat. No. 3,477,919 teaches a method for purifying propylene oxide contaminated with impurities such as methyl formate which boil near propylene oxide. The methyl formate impurity is removed from the contaminated propylene oxide by reaction with an aqueous slurry of calcium hydroxide.

U.S. Pat. No. 2,622,060 teaches a process for separating propylene oxide from a crude reaction mixture by treatment with an aqueous alkali metal hydroxide solution.

U.S. Pat. No. 2,550,847 teaches a process for the purification of propylene oxide in a crude reaction mixture containing methyl formate by subjecting the mixture to strong agitation with an aqueous solution of an alkaline saponifying agent.

U.S. Pat. No. 3,350,417 teaches a process for purifying propylene oxide comprising parallel and serial stages of distillation and a caustic treatment to simultaneously aldolize acetaldehyde and saponify methyl formate. The solvent used in the reaction step is removed before subsequent caustic treatment.

U.S. Pat. No. 4,691,034 removes methyl formate from propylene oxide by contact with an aqueous calcium hydroxide slurry to which a solubilizer has been added. U.S. Pat. No. 4,691,035 removes methyl formate from propylene oxide by contact with a base such as sodium hydroxide in water and glycerol.

U.S. Pat. No. 4,692,535 shows the removal of high molecular weight ethers from propylene oxide by treatment with an absorbent such as activated carbon.

Despite the efforts of prior workers, work has continued in an effort to further improve the separation of contaminating impurities such as methyl formate from lower alkylene oxides such as propylene oxide.

BRIEF DESCRIPTION OF THE INVENTION

In accordance with the present invention, it has been found that lower alkylene oxides having 2 to 4 carbon atoms, particularly propylene oxide, containing methyl formate impurity can be purified by contact with a basic ion exchange resin.

DETAILED DESCRIPTION OF THE INVENTION

This invention is applicable to the purification of propylene oxide prepared, for example, by reaction of an organic hydroperoxide with propylene and containing methyl formate contaminant, illustratively in amounts of 50 to 1600 ppm by weight, usually 100 to 800 ppm.

In accordance with the present invention, a liquid mixture of alkylene oxide and methyl formate contaminant is contacted with solid basic ion exchange resin such as Rohm and Haas' Amberlyst A-21 weak-base ion exchange resin. As a result of this contact, methyl formate is converted to methanol while the formic anion is exchanged with the resin anions and absorbed in the resin. Alkylene oxide essentially free of methyl formate is recovered and methanol, formed during the contact, is readily separated. The ion exchange resin can be completely regenerated by contact with aqueous base such as aqueous sodium hydroxide, calcium hydroxide, potassium hydroxide or the like after the formate removal function of the resin has decreased to an unsatisfactory level.

While not intending to be bound by theory, it is believed that the methyl formate impurity reacts with water, which is normally present in at least trace quantities in the alkylene oxide or which is formed by reaction of acid impurities with the anion exchange resin, to form methanol and formic acid. In especially preferred practice of the invention, the alkylene oxide feed to the anion exchange resin contact contains at least the stoichiometric amount of water necessary to react with the contained methyl formate impurity. Such water can be provided by addition thereof where the impure alkylene oxide does not contain sufficient water, although normally methyl formate containing alkylene oxide feed streams produced by conventional processes contain adequate levels of water for practice of the invention. Generally, excessive amounts of water, e.g. ten times the stoichiometric amount or more, are not advantageous.

The invention may be carried out in a continuous or batch-wise fashion. Continuous operation is preferred as is the use of a plurality of ion exchange resin contact zones with one zone being in use while a second is being regenerated. The use of three contact zones is particularly preferred, with two zones in use at the same time, one a lead contact zone and the second a polishing zone, while the third zone is being regenerated.

Conditions for the contact involve temperatures in the range of about 10° C. to 50° C., preferably 15° C. to 25° C., although temperatures outside these ranges can be used.

Ion exchange resins which are employed in practice of the invention are basic anion exchange resins which are well known articles of commerce. Both strong-base resins and weak-base resins can be used, although weak-base resins are preferred by reason of higher capacity.

Strong-base resins can be produced by the reaction between chlormethylated styrene-DVB copolymer and a tertiary amine such as trimethyl amine, which results in a resin with quaternary ammonium groups.

The principal types of weak-base anion exchangers are amine derivatives of styrene-DVB copolymers, epichlorohydrin-amine condensation products, and amine derivatives of phenol-formaldehyde products, and may contain primary, secondary or tertiary amine groups, or mixtures of some or all of these groups.

Weak-base styrene-DVB resins can be made, for example, by aminating chloromethylated copolymer in much the same way that strong-base styrene-DVB resins are made, except that primary or secondary amines are generally used instead of a tertiary amine.

U.S. Pat. Nos. which describe the preparation of basic anion resins useful in the present invention include: U.S. Pat. Nos. 4,025,467, 3,791,996, 3,817,878, 3,346,516, 4,082,701, 3,843,566, 3,813,353, 3,812,061, 3,882,053, 3,793,273, 3,296,233, 3,108,922, 3,005,786, 3,637,535 and 4,052,343.

The following examples illustrate the invention:

EXAMPLE 1

Twenty grams of Rohm and Haas' Amberlyst A21 weak base anion exchange resin, a styrene/divinyl benzene resin with dimethyl amine functional groups, are placed in a 1.27 centimeter inner diameter and 30 centimeters long glass column. The depth of the resin bed is 24 centimeters and the total resin volume is 30 cubic centimeters. A crude propylene oxide feed containing 450 ppm methyl formate, 0.1 wt. % water and other oxygenate and hydrocarbon impurities is fed to the bottom of the column at a volumetric flow rate of 120 cc/hr. The experiment is conducted at ambient temperature and atmospheric pressure. Discrete effluent samples are collected from the top of the column at predetermined intervals, and the samples are analyzed for methyl formate concentration by a gas chromatograph. The results show that for an accumulative effluent volume of about 2000 cc., no methyl formate is detected in the propylene oxide effluent steam. The methyl formate concentration breakthrough or leakage occurs after about 17 hours of continuous operation. After 25 hours of operation with a total effluent volume of about 3000 cc, the methyl formate concentration in the propylene oxide effluent stream is 60 ppm. After 33 hours of operation or an effluent volume of about 4000 cc, the methyl formate concentration in the propylene oxide effluent stream is 150 ppm, and the resin is regenerated.

EXAMPLE 2

After completion of the experiment described in Example 1, the ion exchange column is drained to remove the excess of propylene oxide and the resin is regenerated by feeding a 4 wt. % sodium hydroxide aqueous solution from the top of column at a volumetric flow rate of 60 cc/hr for two hours at ambient temperature and atmospheric pressure. This step is then followed by water rinse of the bed at 60 cc/hr at ambient temperature for one hour and a nitrogen (50° C.) purge step to dry the resins.

The experiment described in Example 1 is then repeated. No methyl formate is detected for the first 1950 cc of propylene oxide effluent. About 55 ppm and 170 ppm of methyl formate are detected for the accumulated effluent volumes of 3000 cc and 4000 cc, respectively.

What is claimed is:

1. The method of purifying lower alkylene oxide containing a contaminating amount of methyl formate which comprises contacting a mixture of the alkylene oxide, and the methyl formate contaminant with a basic ion exchange resin selected from the group consisting of weak base anion exchange resins containing amine groups and strong base anion exchange resins containing quaternary ammonium groups and separating alkylene oxide having a reduced content of methyl formate.

2. The method of claim 1 wherein said alkylene oxide is propylene oxide.

3. The method of claim 1 wherein said basic ion exchange resin is a weak-base anion exchange resin.

4. The method of claim 1 wherein said mixture contains at least the stoichiometric amount of water necessary to react with the methyl formate.

5. The method of purifying lower alkylene oxide containing a contaminating amount of methyl formate which comprises contacting a mixture of the alkylene oxide and the methyl formate contaminant with a basic ion exchange resin, selected from the group consisting of weak base anion exchange resins containing amine groups and strong base anion exchange resins containing quaternary ammonium groups separating alkylene oxide having a reduced content of methyl formate, and regenerating the said resin by contact with aqueous sodium hydroxide.

6. The method of purifying impure propylene oxide containing 50 to 1600 ppm by weight of methyl formate which comprises contacting said impure propylene oxide with a basic ion exchange resin selected from the group consisting of weak base anion exchange resins containing amine groups and strong base anion exchange resins containing quaternary ammonium groups and separating propylene oxide having a reduced content of methyl formate.

7. The method of claim 6 wherein the basic ion exchange resin is a weak-base anion exchange resin.

8. The method of claim 6 wherein the basic ion exchange resin is Amberlyst A-21.

* * * * *